(12) United States Patent
Ferrell

(10) Patent No.: US 6,944,097 B1
(45) Date of Patent: Sep. 13, 2005

(54) METHOD AND DEVICE FOR MEASURING CAVITATION

(75) Inventor: Gary W. Ferrell, Half Moon Bay, CA (US)

(73) Assignee: Sez America, Inc., Mountain View, CA (US)

(*) Notice: Subject to any disclaimer, the term of this patent is extended or adjusted under 35 U.S.C. 154(b) by 0 days.

(21) Appl. No.: 09/614,485

(22) Filed: Jul. 10, 2000

(51) Int. Cl.[7] ............................................. G01N 29/02
(52) U.S. Cl. ....................................... 367/131; 73/590
(58) Field of Search ................... 367/13, 131; 73/1 D, 73/1.82, 1.83, 590, 587

(56) References Cited

U.S. PATENT DOCUMENTS

| | | | | |
|---|---|---|---|---|
| 3,240,674 A | * | 3/1966 | Ledwidge | 73/590 |
| 3,381,525 A | * | 5/1968 | Kartluke et al. | 73/590 |
| 4,564,422 A | * | 1/1986 | Simoneau et al. | 204/400 |
| 4,763,525 A | * | 8/1988 | Cobb | 73/599 |
| 5,074,150 A | * | 12/1991 | Tirelli et al. | 73/590 |

* cited by examiner

Primary Examiner—Ian J. Lobo
(74) Attorney, Agent, or Firm—Schneck & Schneck; Thomas Schneck; Gina McCarthy

(57) ABSTRACT

A method, probe, and system for detecting presence of cavitation in a fluid and measuring cavitation density and intensity of a specific locale in the fluid. A first cavitation void and associated energy perturbation, produced in a first fluid, moves within the first fluid and is received at a very thin plate, which separates the first fluid from a second fluid and is part of a light-proof chamber containing the second fluid. An energy perturbation in the first fluid is received at the thin plate and produces at least one cavitation void or associated energy perturbation in the second fluid; and the energy perturbation in the second fluid is eventually converted into an electromagnetic signal. This signal is received by a photomultiplier and converted to an electronic signal that indicates the presence of cavitation. The system can distinguish between cavitation voids produced at one location and/or time interval and voids produced at another location and/or another time interval.

20 Claims, 2 Drawing Sheets

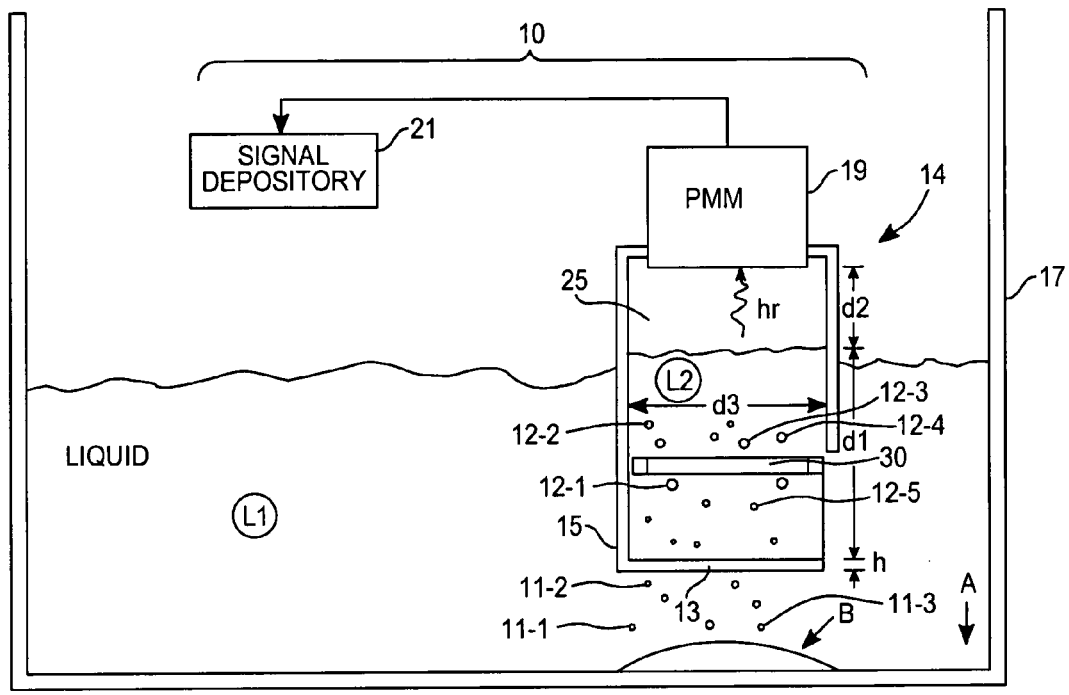
Fig._3
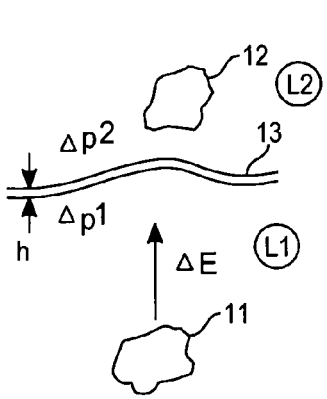
Fig._1
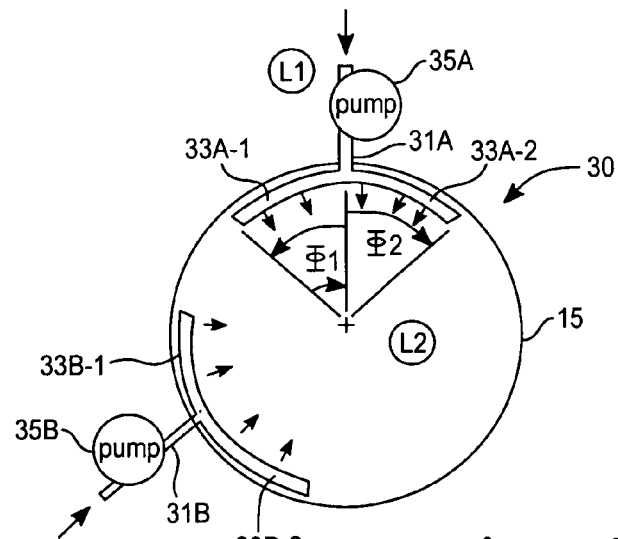
Fig._4
Fig._2

METHOD AND DEVICE FOR MEASURING CAVITATION

FIELD OF THE INVENTION

This invention relates to testing for the presence of, and the frequency of occurrence of, cavitation in a fluid. The present invention provides measurement of the cavitation density and/or intensity of a selected volume in a fluid.

BACKGROUND OF THE INVENTION

Cavitation in a liquid, with a corresponding release of sound energy and/or light energy, is a common occurrence where a perturbing force is present in the liquid. This force can arise from a locally random perturbation, such as a stirring motion or similar action introduced at selected portions (less than all) of the liquid; or the force can arise from perturbations that are coherent over short distances, such as a liquid perturbation intentionally introduced by a transducer immersed in the liquid. One problem is discrimination of the energy pulses produced by the perturbation of interest from energy pulses introduced by other agencies that are not of interest. Since about 1920, it has been known that one or more electromagnetic pulses are released when a cavitation void or bubble collapses, and that the pulse(s) of energy released varies with the degree of vacuum in the void. In the book *Sonoluminescence and Sonochemistry* edited by Lawrence A. Crumm et al, Kluwer Academic Publishers, Dordrecht, 1999, several workers discuss some of the problems and interferences that must be dealt with in probing a given liquid for cavitation action.

One particular use of cavitation is in combination with the amplitude and frequency of sonic vibration generated by ultrasonic and megasonic cleaners to remove particles on silicon wafers and other semiconductor surfaces. Cavitation is the rapid formation and explosion of tiny gas bubbles in a liquid due to the pressure waves generated by a vibrating transducer in a cleaner. Particle removal can be accomplished without surface damage when cavitation occurs uniformly across the wafer surface and its density is controlled. However, in many cavitation systems cavitation occurs non-uniformly, often at certain specific sites on the wafer, leading to pitting and damage. There is currently no means for measuring cavitation uniformity or density in the vicinity of specific sites on the wafer in real time.

What is needed is a system that (1) provides an accurate measurement of the number of cavitation events present in a selected volume of a liquid and (2) discriminates against, or substantially eliminates, the effect of cavitation events that occur elsewhere, not within the selected volume. Preferably, the system should be flexible enough to allow location dependent cavitation probing and should provide compensation for cavitation events of interest that occur within the selected volume but are not sensed by the probe apparatus, due to physical or geometrical constraint.

SUMMARY OF THE INVENTION

These needs are met by the invention, which provides a system in which effects of cavitation that occurs in a first portion of a selected volume are transferred into a second portion of the selected volume that is protected from receipt of interference effects from perturbing forces that are not of interest. In one embodiment, a "dark chamber" is created by a container having a very thin bottom plate that permits transfer of sound energy with relatively little attenuation through the thin plate. The dark chamber is partly immersed in a first selected liquid, and the chamber interior contains a second selected liquid, which may be but need not be the same as the first selected liquid. At the top or one or more sides of the interior of the dark chamber, a photomultiplier module (PMM) is positioned to receive photons produced by cavitation within the second liquid and to convert these photons to electronic pulses that are received and sensed by a pulse sensor that has a relatively short inactivation time. The PMM does not fully enclose the second liquid within the dark chamber interior, and a geometric compensation factor is applied to provide a more accurate estimate of the total number of photons produced within the dark chamber, from knowledge of the number of photons received and converted by the PMM.

By varying the diameter of the dark chamber, which is preferably approximately cylindrical in shape, the number of cavitation events occurring in the first liquid adjacent to the thin plate can be estimated at different locations within the first liquid. An estimate of the location-dependence of cavitation can be made, in which cavitation in each of two or more adjacent regions with corresponding projected areas as small as 0.1 $cm^2$ can be distinguished from each other.

The present invention provides a method of measuring cavitation in a fluid. The method includes the steps of: sensing energy pulses associated with a plurality of cavitation events in a selected volume of the fluid; and discriminating against cavitation events that occur in the fluid outside the selected volume.

A method of mapping the distribution of cavitation events within a selected volume of a fluid is also provided. The method includes the steps of: sensing energy pulses associated with a plurality of cavitation events in a selected volume at a first location within the fluid; sensing energy pulses associated with a plurality of cavitation events in a selected volume at a second location within the fluid; and identifying by three dimensional coordinates within the fluid the specific locations of the first and second selected volumes and the respective cavitation events for each of the selected volumes.

The present invention includes a probe for detecting the presence of cavitation in a fluid. The probe includes a first selected fluid, in which a first energy perturbation, associated with a first cavitation void, is provided. A substantially light-proof container, containing a selected second fluid and at least partly immersed in the first fluid, the container having a thin plate, with a thickness no greater than about 0.25 mm preferably, positioned on a container wall that separates the first and second fluids, whereby the first energy perturbation, when received at the thin plate, produces a second energy perturbation, associated with a second cavitation void, in the second fluid. A photomultiplier, positioned adjacent to or within the container to receive an electromagnetic energy pulse when the second cavitation void collapses within the second fluid. The inventive system includes a signal processor, connected to the photomultiplier, that receives an electronic signal when the photomultiplier receives an electromagnetic signal.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 1 illustrates an effect of cavitation (bubble implosion) and sonic energy production near a very thin energy transfer plate;

FIG. 2 is a graphical view of a sonic pressure pulse that might be produced at one location by cavitation at an adjacent location;

FIG. 3 is a schematic view of an embodiment of apparatus for practicing the invention;

FIG. 4 illustrates in more detail a liquid admission and light baffle control device that may be used as part of the system in FIG. 2.

DETAILED DESCRIPTION OF THE INVENTION

Figure 5:
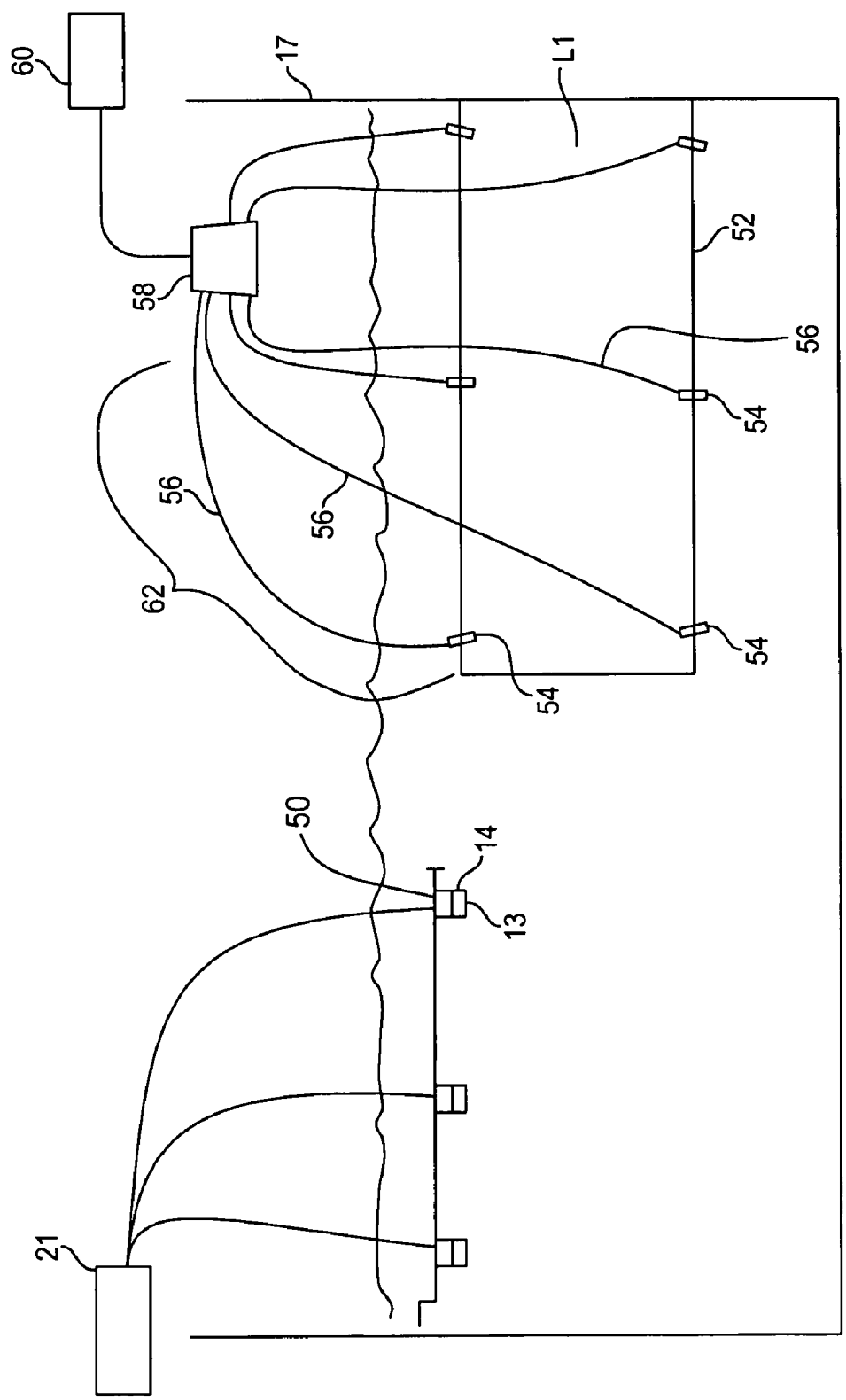
FIG. 5 is schematic view of embodiments of the invention using multiple locations for sensing cavitations.

A cavitation event, illustrated in FIG. 1, involves an implosion of a gas filled or empty, void 11 that is surrounded by a liquid L. The implosion produces a pulse of sonic and/or light energy $\Delta E$ that moves off in some direction. The energy pulse may have a corresponding temporary local temperature rise $\Delta T$ as high as 5500° K, or even higher, and may produce a temporary local pressure rise $\Delta p1$ (+) as large as 50–150 atmospheres, or even higher, followed by a somewhat larger temporary pressure reduction $\Delta p\,1$ (−), as illustrated graphically in FIG. 2. If the cavitation void or associated energy pulse 11 occurs adjacent to, and is received by, a very thin plate 13, shown in FIG. 1, with a plate thickness h of the order of a fraction of a millimeter (h 0.025–0.25 mm, preferably no more than 0.125 mm) or less, the plate will temporarily deform in response to receipt of the corresponding energy perturbation (with corresponding pressure increment $\Delta p\,1$, as illustrated in FIG. 2) and will produce a similar (but partly attenuated) void or associated energy pulse 12 and pressure pulse $\Delta p2$ on the opposite side of the thin plate 13. The energy associated with a single void may be in a range 0–100 ergs but is usually smaller, no more than 1 erg. It is suitable to use any membrane or boundary layer for the thin plate 13 which will temporarily deform in response the receipt of the corresponding energy perturbation and produce a similar void or associated energy pulse 12 on the opposite side of the membrane or boundary layer.

FIG. 3 schematically illustrates a system 10 for practicing the invention including a device or probe 14 for sensing cavitation at a specific locale within a fluid. The probe 14 includes a dark chamber 15 has a hollow interior 25, is light-proof, and is partly or fully immersed in a first selected liquid L1 contained in an outer container or housing 17. The dark chamber interior 25 contains a second selected liquid L2 that may be the same as, or may be different from, the first liquid L1. The liquid levels of the first and second liquids, L1 and L2, may be, but need not be, the same. The second liquid L2 may substantially fill, but preferably does not fill, the entire interior of the dark chamber 25. The dark chamber 15 includes a very thin plate 13 (FIGS. 1 and 3), preferably with a thickness of a small fraction of a millimeter (0.025–0.125 mm or less) on at least one surface (shown at the bottom for definiteness in FIG. 3) of the dark chamber 15.

A cavitation void or associated energy pulse 11-i (i=1, 2, 3) is received at the thin plate 13. The pulse energy of the local energy perturbation 11-i is transferred across the thin plate to produce an energy pulse 12-j (j=1, 2, 3, 4) in the second liquid L2 within the dark chamber 15. The associated energy pulse 12-j ultimately produces one or more pulses hv of electromagnetic (em.) energy that propagates within the second liquid and is ultimately received at a photomultiplier module (PMM) 19, which converts most or all of these em. energy pulses to a signal that is received by a signal processor 21 for display and potential analysis and storage.

Optionally, the PMM 19 has a plurality of geographically dispersed em. energy pulse sensors, with each such sensor being connected to one or a few uniquely identifiable sensors within the signal processor 21. With this configuration, the location of each void or associated energy pulse 12-j that arrives at the PMM 19 can be separately determined, to within a small tolerance.

Let d1 and d2 be the distances of the upper surface of the second liquid L2 from the bottom of the dark chamber 15 and from the nearest face of the PMM 19, respectively; and let d3 be the transverse diameter of the dark chamber 15. If the distances d1 and d2 are decreased so that the ratios d1/d3 and d2/d3 are much less than 1 (e.g., =0.1), the location of each void or associated energy pulse 12-j that arrives at the PMM 19 is well correlated with the location of a "source" void or associated energy pulse 11-i tat the thin plate 13 from which the void or associated energy pulse 12-j arose. This approach would allow a reasonably accurate estimate of the location, in the first liquid L1, where the source void or associated energy pulse arose. For example, a perturbed region, such as "A" near a bottom corner of the container 17 may generate 10–100 cavitation voids per unit area of container surface per sec; while a region such as "B" lying away from all edges or boundaries of the container 17 may generate as many as $10^6$–$3\times10^6$ cavitation voids per unit area per sec, especially if the region B is adjacent to an active energy transducer. Further, the spectrum of energy distribution of the voids may differ from one location to another. If the ratios d1/d3 and d2/d3 are kept small enough, the system 10 illustrated in FIG. 3 can be used to estimate the geometric distribution and energy distribution of cavitation voids in the container 17.

The dark chamber 15 is preferably light-proof so that no light source (referred to herein as a "false source"), except a first energy perturbation or pulse 11-i produced in the first liquid L1 adjacent to the thin plate 13, will produce an energy perturbation or pulse 12-j within the second liquid L2 in the dark chamber interior. The system 10 can also estimate a time at which a cavitation void is produced in the first liquid. If the distances d1 and d2 are very small compared to the distance d3, production of a first cavitation void and associated energy perturbation or pulse will produce a second cavitation void and associated energy perturbation or pulse within the second liquid, will produce an electromagnetic pulse hv that appears at the PMM 19, and will produce an electronic signal that is received and processed at the signal processor 21, all within a time interval having a length as short as 1–1,000 nsec. This allows use of the system 10 to study time-dependent production of cavitation voids, as well as to study location-dependent and energy-dependent cavitation voids, in the first liquid.

In a second embodiment of the invention, the electronic signals are integrated over a time interval, with a selected length, such as $\Delta$=1–100 $\mu$sec, or even longer, in order to estimate the number N($\Delta$t) of associated energy perturbations that occur within the dark chamber 15 within the selected time interval. This embodiment is useful where interest centers on the number N($\Delta$t) of associated energy perturbations that occur in a non-infinitesimal time interval, rather than on the μsec-by-μsec development of these energy perturbations.

Where the first liquid and the second liquid are the same, portions of the first liquid L1 can be admitted into the interior of the dark chamber 25, using an apparatus 30, shown in side view in FIG. 3 and in top view in FIG. 4. A portion of the exterior liquid L1 is transported along a tube 31A, through a light-proof aperture into the interior of the dark chamber 25, where the tube intersects a first curvilinear tube 33A-1 and a second curvilinear tube 33A-2, which are oriented along portions of the perimeter of the dark chamber 15, shown as cylindrical in the top view of FIG. 4. The curvilinear tubes 33A-1 and 33A-2 extend along angular sectors defined by $-\Phi 1<=\Phi<=0$ and $0<=\Phi<=\Phi 2$, where the angles $\Phi 1$ and $\Phi 2$ may be, but need not be, equal. One reasonable choice might be $\Phi 1$ approximately equal to $\Phi 2$ approximately equal to 45°. Further, one or more additional liquid delivery tube arrangements 31B/33B-1,33B-2, may also be provided along the perimeter of the dark chamber 15, as illustrated in FIG. 4.

The first liquid L1 enters the dark chamber interior along the tube 31A, splits into a first stream along the tube 33A-1 and a second stream along the tube 33A-2, and is deposited into the second liquid L2 (in directions indicated by the arrows) as the liquid L1 moves along the tubes 33A-1 and 33A-2. The tube 31A is optionally provided with a pump 35A, having a selected pump power, to transport selected portions of the liquid L1 into the dark chamber interior at a selected volume flow rate. Because the transported liquid must turn by approximately 90° before being deposited into the dark chamber interior, the dark chamber 15 remains substantially light-proof with the liquid delivery tube arrangement 31A/33A-1/33A-2 installed on a wall of the dark chamber.

The PMM 19 preferably has a substantially transparent window, such as quartz, through which the PMM receives the em. energy pulses hv as illustrated in FIG. 3. The first liquid and/or second liquid, L1 and/or L2, can be selected from a collection of suitable liquids, including water, deionized water, isopropyl alcohol, ethyl alcohol, methyl alcohol, tetrahydrofuran, acetone, perfluorohexane, hexane, ether, hydrofluoroether and suitable cleaning liquids and rinsing liquids for semiconductor components, such as $NH_4OH$, HCl, $H_2SO_4$, $HNO_3$, $H_2O_2$ and selected surfactants. Preferably, the second liquid L2 is relatively transparent to em. energy pulses hv that lie in an energy range where these pulses are expected to be produced in the second liquid. The dark chamber 15 and the outer container 17 may be constructed from metals or other solid materials that do not react appreciably with the first and/or second liquids, L1 and L2, such as an Al alloy, a carbon composite polyetheretherketone (PEEK), poly(amide-imide) and polyphenylene sulfide (PPS).

As illustrated and described with reference to FIGS. 3 and 4, the inventive system 10 can measure cavitation density and intensity directly and continuously at a specific locale within a fluid. The probe 14 can measure energy pulses from multiple simultaneous or successive cavitation events as they occur in a two or three-dimensional locale within a fluid. The measured cavitation events can occur randomly within a time period or geographically (spatially) within the locale. The present invention also measures the distribution of the cavitations events in the selected volume by occurrence, geographically (spatially), frequency, sonoluminescence, or other electrical or electronic properties.

The probe 14 can have a stationary position within a fluid to monitor cavitation over successive time periods. The time periods can be of the same or varying length. Alternately, the single probe 14 can be moved between multiple specific locales to measure relative cavitation uniformity. Moving the probe 14 between different specific locales within liquid L1 in container 17 to measure relative cavitation provides a map of cavitation density and intensity in three spatial dimensions and time. At a constant amplitude and frequency, cavitations within the container 17 can be easily measured and displayed as a three-dimensional map.

Preferred embodiments for measuring or monitoring cavitation events occurring at different multiple locales with a fluid are illustrated in FIG. 5. A first array 50 of individual probes like 14 are affixed in a stationary position relative to one another, but not necessarily in a fixed position relative to the container 17. The first array 50 can be moved within the container if desired. Each of the individual probes like 14 transmit a signal to the signal processor 21. A single container 17 can have multiple arrays like 50 therein.

Another preferred embodiment using simultaneous, multiple sensing points for cavitation events uses a second array 52 of individual thin plates 54 as described above in reference to thin plate 13. Each thin plate 54 terminates the end of a dark chamber 56 as described in reference to dark chamber 15. At each sensing point for cavitation events, the energy pulses from the local energy perturbation is transferred across the respective thin plates 54 within the respective dark chambers 56. The energy pulses are remotely received by a PMM 58 that converts the energy pulses to a signal transmitted to a signal processor 60 for display and potential analysis and storage. Each of the thin plates 54 and dark chambers 56 can be contained within a fiber optic 62, wave channel, or the like, which are impervious to external light. The PMM 58 can correlate each measured energy pulse with the appropriate one of the thin plates 54 that was the source.

The present invention includes a probe which includes a light-proof container has at least one container wall that is constructed of a material drawn from the group of materials consisting of an Al alloy, a carbon composite polyetheretherketone (PEEK), poly(amide-imide) and polyphenylene sulfide (PPS). More preferably, the thin plate has a thickness no greater than about 0.125 mm. The electronic signal is received by the signal processor in a time interval that ends no later than about 1000 nsec after the second energy perturbation is produced in the second fluid. At least one of the photomultiplier and the signal processor detects a number of the electronic signals that occur in a time interval of length in a selected range 1–1000 msec. The first energy perturbation is provided with an energy level no greater than about 100 ergs. At least one of the first fluid and the second fluid is selected from a group of fluids consisting of water, deionized water, isopropyl alcohol, ethyl alcohol, methyl alcohol, tetrahydrofuran, acetone, perfluorohexane, hexane, ether, hydrofluoroether, $NH_4OH$, HCl, $H_2SO_4$, $HNO_3$ and $H_2O_2$. The first fluid and the second fluid are selected to be the same fluid. The first fluid and the second fluid are selected to be different fluids.

As used herein, the term fluid includes any material or substance that changes shape or direction uniformly in response to an external force imposed upon it. The term is not limited to liquids, gases, or finely divided solids. The term liquid refers to an amorphous form of matter intermediate between gases and solids in which molecules are much more highly concentrated than in gases buy much less concentrated than in solids.

One preferred application of the present invention is to measure and correlate the ability of ultrasonic and megasonic cleaners to remove particles on silicon wafers and other semiconductor surfaces. The present invention can provide the information on the uniformity of cavitation and cavitation density necessary for efficient particle removal without causing surface damage. Furthermore, the particle removal process can be monitored in real time.

Another preferred application is the monitoring of chemical processes that involve any type of cavitation. The present invention allows in situ, real time measurement of localized energy perturbations. The correlation between the status or rate of progress of a chemical process and cavitation density and/or intensity can be used to remotely monitor the completion or efficiency of the chemical process.

The present invention provides an accurate measurement of the number of cavitation events present in a selected volume of a liquid and discriminates against, or substantially eliminates, the effect of cavitation events that occur elsewhere, not within the selected volume. The system is sufficiently flexible to allow location dependent cavitation probing and provides compensation for cavitation events of interest that occurs within the selected volume but is not sensed by the probe apparatus, due to physical or geometrical constraint.

While the invention has been particularly shown and described with reference to a preferred embodiment, it will be understood by those skilled in the art that various changes in form and detail may be made therein without departing from the spirit and scope of the invention.

What is claimed is:

1. A method of measuring cavitation in a fluid, the method comprising:
   sensing energy pulses on one side of a deformable plate associated with a plurality of cavitation events occurring on another side of the deformable plate in a selected volume of the fluid; and
   discriminating against cavitation events that occur in the fluid outside the selected volume.

2. The method of claim 1 wherein the method includes measuring the cavitation density of the selected volume in the fluid.

3. The method of claim 1 wherein the method includes measuring the cavitation intensity of the cavitation events in the selected volume in the fluid.

4. The method of claim 1 wherein the sensing step includes directly detecting the energy pulses associated with the cavitation events in the selected volume in the fluid.

5. The method of claim 1 wherein the sensing step includes continuously detecting the energy pulses associated with the cavitation events in the selected volume in the fluid.

6. The method of claim 1 wherein the method includes measuring the distribution of the cavitation events in the selected volume in the fluid.

7. The method of claim 1 wherein the sensing step includes the energy pulses associated with the cavitation events are generated in a spatially random distribution within the selected volume in the fluid.

8. A method of mapping the distribution of cavitation events within a selected volume of a fluid, the method comprising:
   sensing energy pulses associated with a plurality of cavitation events in a selected volume at a first location within the fluid;
   sensing energy pulses associated with a plurality of cavitation events in a selected volume at a second location within the fluid; and
   identifying by three dimensional coordinates within the fluid the specific locations of the first and second selected volumes and the respective cavitation events for each of the selected volumes.

9. The method of claim 8 wherein the method includes measuring the cavitation density of the selected volume in the fluid.

10. The method of claim 8 wherein the method includes measuring the cavitation intensity of the cavitation events in the selected volume in the fluid.

11. The method of claim 8 wherein the sensing steps are performed simultaneously.

12. A method for detecting the presence of cavitation in a fluid, the method comprising:
   receiving at a thin plate a selected first energy perturbation associated with a cavitation in a first selected fluid, the thin plate separating the first selected fluid from a second selected fluid, and thereby creating a second energy perturbation in the second fluid;
   converting the second energy perturbation into a least one electromagnetic pulse of energy;
   receiving a signal representing the at least one electromagnetic pulse at a photomultiplier positioned adjacent to a selected surface of the second fluid, thereby creating an electronic signal; and
   interpreting presence of the electronic signal as indicating that a cavitation void has occurred in the first fluid.

13. The method of claim 12, further comprising providing a light-proof container, having the thin plate on at least one wall, to hold the second fluid.

14. The method of claim 13, further comprising choosing the light-proof container to have at least one container wall that is constructed of a material drawn from the group of materials consisting of an Al alloy, a carbon composite polyetheretherketone (PEEK), poly(amide-imide) and polyphenylene sulfide (PPS).

15. The method of claim 12, further comprising receiving the first energy perturbation at the thin plate having the plate thickness no greater than about 0.25 mm.

16. The method of claim 12, further comprising detecting the electronic signal in a time interval that ends no later than about 1000 nsec after providing the perturbation in the first fluid.

17. The method of claim 12, further comprising detecting a number of the electronic signals that occur in a time interval of length in a selected range 1–1000 msec.

18. The method of claim 12, further comprising providing the first energy perturbation with an energy level no more than about 100 ergs.

19. The method of claim 12, further comprising selecting at least one of the first fluid and the second fluid from a group of fluids consisting of water, deionized water, isopropyl alcohol, ethyl alcohol, methyl alcohol, tetrahydrofuran, acetone, perfluorohexane, hexane, ether, hydrofluoroether, $NH_4OH$, $HCl$, $H_2SO_4$, $HNO_3$ and $H_2O_2$.

20. The method of claim 12, further comprising providing the same fluid for the first fluid and the second fluid.

* * * * *